United States Patent [19]

Kofod

[11] 4,265,884
[45] May 5, 1981

[54] THERAPEUTICALLY ACTIVE POLYPEPTIDES OR ACID ADDITION SALTS THEREOF AND A PROCESS FOR PRODUCING SUCH COMPOUNDS

[75] Inventor: Hans Kofod, Lyngby, Denmark

[73] Assignee: Nordisk Insulinlaboratorium, Gentofte, Denmark

[21] Appl. No.: 78,425

[22] Filed: Sep. 24, 1979

[30] Foreign Application Priority Data

Sep. 28, 1978 [DK] Denmark .......................... 4304/78
Sep. 5, 1979 [DK] Denmark .......................... 3710/79

[51] Int. Cl.$^3$ ..................... A61K 37/00; C07C 103/52
[52] U.S. Cl. ........................... 424/177; 260/112.5 R
[58] Field of Search ................ 424/177; 260/112.5 R

[56] References Cited

U.S. PATENT DOCUMENTS

| 4,086,220 | 4/1978 | Schlatter | 424/177 |
| 4,107,158 | 8/1978 | Lefrancier | 424/177 |

OTHER PUBLICATIONS

J. E. Jorpes and V. Mutt, "Secretin, Cholecystokinin, Pancreozymin and Gastrin", Springer-Verlag, Berlin (1973), pp. 30 and 31.

Itakura, K. et al., SCIENCE, vol. 198, (1977), pp. 1056-1063.

Enk, B. et al., "Ugeskrift for Laeger", (Weekly publication for Doctors), 134, No. 49, (1972), pp. 2577-2580.

Primary Examiner—Delbert R. Phillips
Attorney, Agent, or Firm—Ladas & Parry

[57] ABSTRACT

Polypeptide derivatives of the formula:

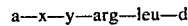

$$a-x-y-arg-leu-d$$

wherein
x represents a bond, a single amino acid or a peptide having up to 10 amino acids in the chain,
y represents gln- glu or glu,
a represents hydrogen or a small protective group for the α-amino group in the N-terminal amino acid,
d represents —NR$^1$R$^2$, wherein R$^1$ and R$^2$ are selected from the group consisting of hydrogen, C$_1$-C$_6$ alkyl and C$_3$-C$_8$ cycloalkyl, or R$^1$ and R$^2$ together with the attached nitrogen atom form a heterocyclic group optionally containing an additional hetero atom, or
d represents —OR$^3$, wherein R$^3$ is selected from the group consisting of hydrogen, C$_1$-C$_6$ alkyl, C$_3$-C$_8$ cycloalkyl, benzyl, substituted benzyl, phenacyl, phthalimidomethyl, β-methylthioethyl, and 4-picolyl or acid addition salts of such peptides, may be produced by peptide synthesis methods known per se.

The polypeptides potentiate the glucose stimulated secretion of insulin from Langerhans's islets.

3 Claims, No Drawings

THERAPEUTICALLY ACTIVE POLYPEPTIDES OR ACID ADDITION SALTS THEREOF AND A PROCESS FOR PRODUCING SUCH COMPOUNDS

The present invention relates to a group of new, therapeutically active peptides, and a process for producing them. The present peptides are characteristic in that in vitro they potentiate the glucose stimulated secretion of insulin from Langerhans's islets.

The present peptides may be described as follows:

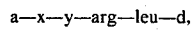

a—x—y—arg—leu—d, wherein x may represent a bond, a single amino acid (e.g. leu, ile, ala, gly, ser, val, thr, lys, arg, asp, asn, glu, gln, met, phe, tyr, trp or his) or peptides having up to 10 amino acids in the chain (e.g. arg-leu, ala-arg-leu, ser-ala-arg-leu, asp-ser-ala-arg-leu or leu-ser-arg-leu-arg-asp-ser-ala-arg-leu), y represents gln, glu or

which is ring-closed glutamic acid (pyroglutamic acid), a represents hydrogen or a small protective group for the α-amino group in the N-terminal amino acid, e.g. acetyl or propionyl, etc., d may represent —NR$^1$R$^2$, wherein R$^1$ and R$^2$ are selected from the group consisting of hydrogen, C$_1$-C$_6$ alkyl and C$_3$-C$_8$ cycloalkyl (e.g. methyl, ethyl, propyl, isopropyl, butyl, tertiary butyl, pentyl, hexyl, cyclopentyl, cyclohexyl, etc.). R$^1$ and R$^2$ may also be linked together so as to form a cyclic group having at least 1 hetero atom, i.e. the amide bonded nitrogen atom (e.g. pyrrol, pyrroline, pyrrolidine, piperidine, etc.), said group optionally containing an additional hetero atom, such as nitrogen, oxygen, or sulfur (e.g. pyrimidine, morpholine or thiomorpholine), d may also represent —OR$^3$, wherein R$^3$ is selected from the group consisting of hydrogen, C$_1$-C$_6$ alkyl (methyl, ethyl, propyl, isopropyl, butyl, isobutyl, tertiary butyl, pentyl, hexyl, etc.), C$_3$-C$_8$ cycloalkyl (cyclopentyl, cyclohexyl, cycloheptyl, etc.), benzyl, phenacyl, phthalimidomethyl, β-methylthioethyl, 4-picolyl, and substituted benzyl, wherein the substituents are at least one of the following groups: nitro, methoxy, methyl, halogen, (e.g. p-methoxybenzyl, 2,4-dimethoxybenzyl, etc.). R$^3$ is preferably C$_1$-C$_6$ alkyl, benzyl or substituted benzyl.

The invention also relates to acid addition salts of said peptides with acids acceptable to the organism, such as HCl or CH$_3$COOH, and capable of forming salts with the peptides.

The present peptides and peptide derivatives may be produced in a manner known per se, single amino acids or peptides, appropriately protected, being coupled to single amino acids or peptides, likewise appropriately protected, by means of carboxylic acid activating substances, as described in Houben-Weyl: Methoden der organischen Chemie 15/2, Synthesen von Peptiden, p. 2-364 (1), e.g. by means of dicyclohexylcarbodiimide, N-ethyl-N'-(dimethylaminopropyl)-carbodiimide, o-nitrophenol, p-nitrophenol, pentachlorophenol with or without addition of catalyzing substances.

Moreover, the peptides may be produced by enzymatic catalysis, e.g. as described by Widmer, F. and Johansen, J. T. (3) or by means of the gene of the individual peptides by the so-called gene manipulation, e.g. as described by Itakura, K. et al. (4).

Trifunctional amino acids forming part of the peptides may either appear unprotected in the side chain group or be protected. N$^G$ which refers to side chain nitrogen in arginine may e.g. be protected with one of the following groups: H$^+$, —NO$_2$, tosyl, t-butyloxycarbonyl or carbobenzoxy. The hydroxy group in serine may e.g. be protected by t-butyl ether or benzyl ether during the synthesis, and the β-acid group in aspartic acid may be protected as benzyl ester. Generally all the constituent, functional groups may be protected in a manner known per se. Primarily, protective groups are used which may be cleaved hydrogenolytically.

The α-amino groups may be protected by e.g. t-butyloxycarbonyl, carbobenzoxy, adamantyloxycarbonyl or isoborneyloxycarbonyl. Primarily, t-butyloxycarbonyl is used.

A plurality of the present peptides are sequencies or derivatives of sequences of the intestinal hormone secretin.

Secretin primarily affects the exocrinic pancreas, but it has been demonstrated that secretin in pharmacological dosages potentiate the secretion of insulin, without affecting the blood sugar level though, Enk et al. (5).

It has now surprisingly been found that the present peptides, which structurally are derived from secretin, have an insulin liberating effect, while Jorpes et al. (2) state that the whole secretin molecule must be present to give biological activity. Moreover, under the same in vitro conditions as for the present peptides it has not been possible to make secretin affect the insulin liberation from isolated Langerhans's islets.

The U.S. Pat. No. 4,086,220 describes, however, that the secretin fragments 1-15, 1-16, 1-17, and 1-18 like secretin possess biological activity on the exocrinic pancreas.

The effect just mentioned may in particular be used for treating diabetics who themselves have lost the ability to liberate insulin from the Langerhan's islets.

In vitro determination of the effect or the peptides on the glucose stimulated insulin secretion was carried out on Langerhans's islets isolated by collagenase technique and preincubated 24 hours at 37° C. Secretion tests were conducted with 10 mM of glucose and three peptide concentrations.

| Peptide | $5 \times 10^{-2}$ mM | $5 \times 10^{-1}$ mM | 5mM |
|---|---|---|---|
| 1 | 144 | 113 | 151 |
| 2 | 122 | 132 | 252 |
| 3 | 124 | 127 | 240 |
| 4 | 135 | 120 | 153 |
| 5 | — | 140 | 268 |
| 6 | — | 110 | 142 |

1. gln—arg—leu—OMe, 2HCl

2.  glu—arg—leu—OMe, HCl
3. leu—gln—arg—leu—OMe, 2HCl
4. arg—leu—gln—arg—leu—OMe, 3HCl
5. ser—ala—arg—leu—gln—arg—leu—OMe, 3HCl
6. asp—ser—ala—arg—leu—gln—arg—leu—OMe, 3HCl All peptides have been tested in the form of their hydrochlorides together with 10 mmolar glucose, and the value is calculated as a percentage of the effect of 10 mmolar glucose alone.

The peptides may be administered as injection preparations or per os.

The preparation of the present peptides is illustrated by the following examples.

EXAMPLES

All the amino acids mentioned in the specification are the naturally occurring L-forms and their abbreviations follow the 3-letter abbreviations laid down by IUPAC-IUB.

Further, the following abbreviations are used.

| BOC: | t.-butyloxycarbonyl | TLC: | thin layer chromatography |
|---|---|---|---|
| DMF: | dimethylformamide | AcOH: | acetic acid |
| TEA: | triethylamine | MeOH: | methanol |
| ONO: | o-nitrophenyl | BAW623: | butanol-1:acetic acid: water = 6:2:3 |
| ONP: | p-nitrophenyl | | |
| EE: | ethylacetate | BAWP: | butanol 1:acetic acid: water:pyridine = 30:6:24:20 |
| Bzl: | benzyl | HBT: | hydroxybenzotriazole |
| TFA: | trifluoroacetic acid | SHI: | chloroform-methanol-acetic acid = 90:5:5 |
| PCP: | pentachlorophenyl | | |
| AAA: | amino acid analysis | DAPECI: | dimethylaminopropyl-ethyl-carbodiimide |

Analyses of amino acids were carried out on Beckman 120C Amino acid Analyzer.

TLC was carried out in BAW (A) and BAWP (B) and SHI (c).

The purity criterion for protected peptides is the presence of only one spot in TLC in liquid A and C.

The following examples are representative of the reactions used.

EXAMPLE 1 asp-ser-ala-arg-leu-gln-arg-leu-OMe, 3HCl

BOC-($NO_2$)arg-leu-OMe 10 g of leu-OMe, HCl were dissolved in 100 ml of $CH_2Cl_2$ to which 8 ml of TEA were added. Then there was added a solution of 16 g of BOC-($NO_2$)arg in 75 ml of $CH_2Cl_2$ and 25 ml of DMF. The mixture was cooled to $-5°$ C., and then 9 g of dimethylaminopropyl-ethyl-carbodiimide, HCl were added. After finished reaction excess of carbodiimide was decomposed with 15% AcOH (150 ml). The mixture was evaporated to an aqueous phase which was shaken up with ethylacetate (3×100 ml), and the ethylacetate was washed with 3×50 ml of 10% citric acid, 3×50 ml of saturated $NaHCO_3$ and 3×50 ml of water. The ethylacetate was evaporated and the product was dried. Yield: 20 g=90%.

BOC-gln-($NO_2$)arg-leu-OMe 2 g of BOC-($NO_2$)arg-leu-OMe were dissolved in 15 ml of TFA and left to stand with stirring for 15 minutes. 125 ml of dry ether were added for precipitation. The precipitate was isolated after 15 minutes' stirring by repeated centrifugations and washings with dry ether. The peptide TFA salt was dissolved in 50 ml of DMF to which there were added 750 μl of TEA and 3 g of BOC-gln-ONP. After 24 hours the reaction was over. The product was evaporated to a yellow oil at a reduced pressure. 50 ml of EE were added, and then excess of BOC-gln-ONP and formed p-nitrophenol were washed out with saturated $NaHCO_3$. The product was precipitated together with a small amount of BOC-gln-ONP after drying with $MgSO_4$ and standing in the cold. Residue of BOC-gln-ONP was washed out by repeated washings of the precipitate with EE. Yield: 2.1 g=82%.

BOC-leu-gln-($NO_2$)arg-leu-OMe 1.5 g of BOC-gln-($NO_2$)arg-leu-OMe were treated for 15 minutes with 15 ml of TFA. 100 ml of dry ether were added for precipitation of the peptide salt. The peptide salt was isolated and purified by repeated washings and centrifugations in dry ether. The peptide TFA salt was dissolved in 15 ml of DMF to which 700 μl of TEA and 3.5 g of BOC-leu-ONP were added. After 24 hours the reaction was terminated, and the product was evaporated to a yellow oil. The oil was dissolved in ethylacetate from which the product was precipitated by addition of ether and standing in the cold. The product was isolated and thoroughly washed with ethylacetate:ether 2:3. Yield: 1.5=84%.

BOC-($NO_2$)arg-leu-gln-($NO_2$)arg-leu-OMe 1 g of BOC-leu-gln-($NO_2$)arg-leu-OMe was treated with 15 ml of TFA for 15 minutes. 100 ml of dry ether were added for precipitation of the peptide TFA salt. The peptide TFA salt was isolated, thoroughly washed with dry ether and dried. The peptide TFA salt was dissolved in 25 ml of DMF to which were added 1 g of BOC-($NO_2$)arg-PCP, 300 mg of HBT and 300 μl of TEA. During the reaction another 300 mg of active ester and TEA were added until basic reaction. After the reaction was terminated the product was evaporated to a yellow oil which was suspended in 100 ml of EE. The EE-phase was washed with water. The EE-phase was evaporated at a reduced pressure, and the residue was dried. Then it was dissolved in 20 ml of EE which was left to stand in the cold. Standing makes the product precipitate in purified form. Yield: 900 mg=70%.

BOC-ala-($NO_2$)arg-leu-gln-($NO_2$)arg-leu-OMe 550 mg of BOC-($NO_2$)arg-leu-gln-($NO_2$)arg-leu-Ome were treated for 15 minutes with 15 ml of TFA. TFA was evaporated at a reduced pressure, and then dry ether was added. The peptide salt was isolated, thoroughly washed with dry ether and dried. The salt was dissolved in 25 ml of DMF to which 500 mg of BOC-ala-ONO and 130 μl of TEA were added. After finished reaction the product was evaporated to an oil which solidified when EE was poured over it. The product was isolated, thoroughly washed with EE and dried. Yield: 440 mg=74%.

BOC-(OBzl)ser-ala-($NO_2$)arg-leu-gln-($NO_2$)arg-leu-OMe 440 mg of BOC-ala-($NO_2$)arg-leu-gln-($NO_2$)arg-leu-Ome were treated for 20 minutes with 15 ml of TFA. TFA was evaporated at a reduced pressure to about 5 ml. 75 ml of dry ether were added, precipitating the peptide salt. The peptide salt was isolated, washed with dry ether and dried. The salt was then dissolved in 20 ml of DMF of which were added 500 mg of BOC-(OBzl)s-er-ONO and 100 μl of TEA. When the reaction was over the product was evaporated to a yellow oil over which EE was poured for precipitating the product, which was isolated and thoroughly washed with EE and dried. Yield: 450 mg=86%.

BOC-($\beta$-Bzl)asp-(OBzl)ser-ala-($NO_2$)arg-leu-gln-($NO_2$)arg-leu-OMe 300 mg of BOC-(O Bzl)ser-ala-($NO_2$)arg-leu-gln-($NO_2$)arg-leu-OMe were treated with 15 ml of TFA for 20 minutes. 100 ml of dry ether were added. The peptide TFA salt was isolated, washed with dry ether and dried. The salt was dissolved in 20 ml of DMF to which 500 mg of BOC-(β-Bzl)-asp-ONO and 50 μl of TEA were added. When the reaction was over the product was evaporated to a yellow oil over which EE was poured to precipitate the product. The product was isolated in pure form by thorough washing with dry ether and subsequent drying. Yield: 300 mg = 85%.

asp-ser-ala-arg-leu-gln-arg-leu-OMe, 3HCl 300 mg of BOC-(β-Bzl)asp-(OBzl)ser-ala-(NO₂)arg-leu-gln-(NO₂)arg-leu-OMe were hydrogenated at 1 atm. with H₂ over Pd/C in 10% AcOH/MeOH. After finished hydrogenation the catalyst was filtered off and washed very thoroughly. The product was evaporated to an oil which was transferred to a dry silica gel column, and the substance was purified on it with 5% AcOH/MeOH. The pure intermediate was treated with 15 ml of 1 N HCl/AcOH for 30 minutes. 100 ml of dry ether were added to precipitate the product. It was thoroughly washed with dry ether. Yield: 200 mg = 85%.

AAA: ala:asp:ser:gln:leu:arg = 1.00:1.05:0.64:0.90:1.96:0.95.

Serine is low due to the hydrolysis method.
TLC: Rf$_{(A)}$ = 0.29 Rf$_{(B)}$ = 0.45.
M.p. (decomp.) = 170°.
Total yield: 20% of the theoretical one.

EXAMPLE 2

The peptides gln-arg-leu-OMe, 2HCl
AAA: glu:leu:arg:NH₃ = 1.05:1.00:0.95:1.13
Theory = 1.00:1.00:1.00:1.00
TLC: Rf$_{(A)}$ = 0.28 M.p. (decomp.) = 125° C.
leu-gln-arg-leu-OMe, 2HCl
AAA: glu:leu:arg:NH₃ = 1.00:2.00:0.93:0.96
Theory = 1.00:2.00:1.00:1.00
TLC: Rf$_{(A)}$ = 0.35
M.p. (decomp.) = 116° C.
arg-leu-gln-arg-leu-OMe, 3HCl
AAA: glu:leu:arg:NH₃ = 1.00:1.95:1.80:0.93
Theory = 1.00:2.00:2.00:1.00
TLC: Rf$_{(A)}$ = 0.31
M.p. (decomp.) = 154° C.
ala-arg-leu-gln-arg-leu-OMe, 3HCl
ser-ala-arg-leu-gln-arg-leu-OMe, 3HCl
AAA: glu:leu:ser:ala:arg:NH₃ = 0.99:1.80:0.73:1.00:1.75:1.00
Theory = 1.00:2.00:1.00:1.00:2.00:1.00
TLC: Rf$_{(A)}$ = 0.27
M.p. (decomp.) = 140° C.
were produced from the corresponding protected peptides, in example 1 by catalytic hydrogenation and subsequent cleavage of the BOC group with 1 N HCl/AcOH.

EXAMPLE 3

The peptides glu-arg-leu-OMe, 2HCl
TLC: Rf$_{(A)}$ = 0.35
M.p. (decomp.) = 135° C.
and

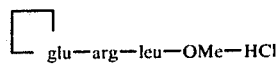
glu—arg—leu—OMe—HCl

AAA: glu:leu:arg = 1.04:1.00:0.94
Theory = 1.00:1.00:1.00
TLC: Rf$_{(A)}$ = 0.40

M.p. (decomp.) = 115° C.
were produced analogously with gln-arg-leu-OMe, 2HCl, in example 1 by replacing BOC-gln-ONP with BOC-(Bzl)glu-ONO and

BOC—glu—ONP, respectively.

Bibliography (1) Houben-Weyl: Methoden der organischen Chemie 15/2, Synthesen von Peptiden, p. 2–364, (1974) Georg Thieme Verlag, Stuttgart.

(2) J. E. Jorpes and V. Mutt: Secretin, Cholecystokinin, Pancreozymin and Gastrin, p. 30 (1973) Springer-Verlag, Berlin.

(3) Widmer, F. and Johansen, J. T., Carlsberg. Res. Commun. Vol. 44, p. 3746 (1979).

(4) Itakura, K. et al., Science 198, p. 1056 (1977).

(5) Enk, B., Kolendorf, K., Deckert, T. —Ugeskrift for Laeger (a weekly publication for doctors), 134, No. 49, p. 2577–80 (1972).

I claim:

1. Polypeptide derivatives of the general formula:

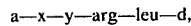
a—x—y—arg—leu—d, wherein
y represents gln, glu or

glu, x represents a bond, a single amino acid selected from the group consisting of leu and ser, or when y is gln x may also represent a peptide having from 2 to 10 amino acids in their naturally occurring L-form in the chain, selected from C₁₀–C₁₉ fragments of secretin, with the proviso that the C-terminal amino acid is always leu 19 (acid number 19 in the secretin sequence), a represents hydrogen or a small protective group for the α-amino group in the N-terminal amino acid, d represents —NR¹R², wherein R¹ and R² are selected from the group consisting of hydrogen, C₁–C₆ alkyl and C₃–C₈ cycloalkyl, or R¹ and R² together with the attached nitrogen atom form a heterocyclic group optionally containing a further hetero atom, or d represents —OR³, wherein R³ is selected from the group consisting of hydrogen, C₁–C₆ alkyl, C₃–C₈ cycloalkyl, benzyl, phenacyl, phthalimidomethyl, β-methylthioethyl, 4-picolyl and substituted benzyl, where the substituents are selected from the group consisting of nitro, methoxy, methyl, and halogen, or acid addition salts of such peptides with acids acceptable to the organism.

2. A polypeptide derivative according to claim 1, wherein x is selected from the group consisting of leu, ser, arg-leu, ala-arg-leu, ser-ala-arg-leu, asp-ser-ala-arg-leu and leu-ser-arg-leu-arg-asp-ser-ala-arg-leu.

3. A pharmaceutical composition useful for potentiating the glucose stimulated secretion of insulin, which composition comprises an effective amount of a polypeptide derivative of the general formula of claim 1 in admixture with a pharmaceutically acceptable non-toxic carrier.

* * * * *